United States Patent [19]
Nonami et al.

[11] Patent Number: 5,711,763
[45] Date of Patent: Jan. 27, 1998

[54] COMPOSITE BIOLOGICAL IMPLANT OF A CERAMIC MATERIAL IN A METAL SUBSTRATE

[75] Inventors: Tohru Nonami; Naoyoshi Satoh, both of Chiba, Japan

[73] Assignee: TDK Corporation, Tokyo, Japan

[21] Appl. No.: 497,037

[22] Filed: Jun. 30, 1995

Related U.S. Application Data

[63] Continuation of Ser. No. 251,635, May 31, 1994, abandoned, which is a continuation of Ser. No. 839,391, Feb. 20, 1992, abandoned.

[30] Foreign Application Priority Data

Feb. 20, 1991 [JP] Japan ................................. 3-045676

[51] Int. Cl.$^6$ ................................................. A61F 2/28
[52] U.S. Cl. ........................... 623/16; 623/11; 433/201.1; 606/76
[58] Field of Search .............................. 433/199.1, 200.1, 433/201.1; 606/76, 77; 623/11, 16

[56] References Cited

U.S. PATENT DOCUMENTS

| | | | |
|---|---|---|---|
| 4,309,488 | 1/1982 | Heide et al. | 606/76 |
| 4,365,356 | 12/1982 | Broemer et al. | 623/16 |
| 4,483,678 | 11/1984 | Nishio et al. | 623/18 |
| 4,652,534 | 3/1987 | Kasuga | 623/18 |
| 4,702,930 | 10/1987 | Heide et al. | 623/16 |
| 4,818,559 | 4/1989 | Hama et al. | 433/173 |
| 4,846,837 | 7/1989 | Kurze et al. | 623/16 |
| 4,857,269 | 8/1989 | Wang et al. | 623/16 |
| 5,263,986 | 11/1993 | Noiles et al. | 623/16 |
| 5,330,826 | 7/1994 | Taylor et al. | 623/16 |
| 5,344,456 | 9/1994 | Nonami et al. | 623/16 |
| 5,360,448 | 11/1994 | Thramann | 606/76 |

FOREIGN PATENT DOCUMENTS

| | | |
|---|---|---|
| 0 006 544 | 1/1980 | European Pat. Off. . |
| 0 023 608 | 2/1981 | European Pat. Off. . |
| 0 280 592 | 8/1988 | European Pat. Off. . |
| WO 87 06842 | 11/1987 | WIPO . |

OTHER PUBLICATIONS

M. Toriyama, et al., pp. 1268–12270, 1991, "Alpha–Tricalcium Phosphate Coating on Titanium".

*Primary Examiner*—Paul B. Prebilic
*Attorney, Agent, or Firm*—Oblon, Spivak, McClelland, Maier & Neustadt, P.C.

[57] ABSTRACT

A composite biotic implant of the invention is prepared by coating a metal substrate with ceramic particles preferably having bio-compatibility, and plastic working the coated substrate to cause plastic deformation of the metal substrate, thereby embedding the ceramic particles in a surface layer of the metal substrate. Optionally, ceramic material having bio-compatibility is coated over the surface of the ceramic particle embedded substrate. A composite implant exhibiting a firm bond is thus obtained.

16 Claims, 9 Drawing Sheets

COMPOSITE BIOLOGICAL IMPLANT OF A CERAMIC MATERIAL IN A METAL SUBSTRATE

This application is a Continuation of application Ser. No. 08/251,635, filed on May 31, 1994, now abandoned, which is a Continuation of application Ser. No. 07/839,391 filed Feb. 20, 1992, now abandoned.

BACKGROUND OF THE INVENTION

1. Field of the Invention

This invention relates to composite bio-active implants including artificial dental roots, artificial dental crowns, artificial bones, and artificial joints, and more particularly, to composite implants having a ceramic layer on a metal substrate wherein the ceramic layer never peels off and which has a desired shape, surface nature and surface precision and a method for preparing such implants in a simple efficient manner by taking advantage of the high plasticity of the metal substrate.

The biotic implants of the present invention are advantageously utilized as implants in the form of bio-replacements or complements to be implanted in living tissues or cavities, for example, artificial dental roots and crowns, artificial bones, artificial joints, bone fillers, artificial blood vessels, etc. as well as living body indwelling medical equipment and implements, for example, dialysis shunts, percutaneous terminals, pacemakers, bio-electrodes, etc., and thus the biotic implants encompass all these elements.

2. Prior Art

There were proposed several composite implants, for example, implants having hydroxyapatite plasma sprayed on metal (Japanese Patent Publication No. 39533/1983), metal implants which are oxidized on the surface and coated with calcium phosphate (Japanese Patent Publication Nos. 6537/1990, 14060/1990, 14061/1990 and 18102/1990), implants having a graded structure (Japanese Patent Application Kokai No. 147455/1988), etc.

These implants, however, have the risk that since the bond between a metal substrate and a ceramic material is established only by chemical reaction at the material interface, the ceramic material can chip away or peel off due to weak bond strength. It is a serious problem that once the ceramic material chips away or peels off, the ceramic layer can peel off over a large extent.

For implants as artificial dental roots, it is important to control the surface nature and roughness of the implants for facilitating their integration to living bones and growth of neoblastic bones. The conventional methods, however, are difficult to achieve desired surface nature while maintaining strength.

SUMMARY OF THE INVENTION

A primary object of the present invention is to eliminate the drawbacks of the prior art implants and to provide an implant having improved strength and surface nature and exhibiting increased initial fixing or rooting forces, that is, bio-compatibility and bio-affinity, preferably bio-activity as well as a method for preparing the same, especially to provide a novel implant comprising a metal substrate and a ceramic material thereon having high peel strength and thus free of cracking and chipping problems as well as a method for preparing the same.

This and other objects are achieved by embedding biocompatible ceramic particles in a metal core by virtue of metal plasticity to induce physical and chemical bonds, thereby providing an implant possessing both strength and bio-compatibility. The present invention is embodied as (1) to (22) defined below.

(1) A composite biotic implant comprising a substrate having ceramic particles embedded in a surface layer thereof.

(2) The composite biotic implant of (1) wherein said metal has a ductility of at least 50% at a temperature corresponding to 70% or less of its melting point.

(3) The composite biotic implant of (1) or (2) wherein said ceramic particles exhibit bio-compatibility.

(4) The composite biotic implant of any one of (1) to (3) wherein said ceramic particles exhibit bio-affinity.

(5) The composite biotic implant of any one of (1) to (4) wherein said ceramic particles have a mean particle size of 1 to 5,000 μm.

(6) The composite biotic implant of any one of (1) to (5) wherein said ceramic particles have an average shape factor of up to 2.

(7) The composite biotic implant of any one of (1) to (6) wherein the embedment of said ceramic particles in the metal substrate is at least 10% of the ceramic particle size.

(8) The composite biotic implant of any one of (1) to (7) wherein the coverage of the biotic contact surface of the metal substrate with said ceramic particles is at least 20%.

(9) The composite biotic implant of any one of (1) to (8) wherein said ceramic particles have a coefficient of thermal expansion which is lower than the coefficient of thermal expansion of the metal substrate multiplied by a factor of 0.5 to 1.5.

(10) The composite biotic implant of any one of (1) to (9) which includes an embedment layer where said ceramic particles are embedded in a surface layer of said metal substrate and a layer of a bio-compatible ceramic material coated over the embedment layer.

(11) The composite biotic implant of any one of (1) to (10) wherein said composite implant has a surface roughness Ra of 1 to 2,000 μm at the outer surface.

(12) The composite biotic implant of (10) or (11) wherein said embedment layer having ceramic particles embedded and said coating layer have a total thickness of 1 to 5,000 μm.

(13) The composite biotic implant of any one of (10) to (12) wherein said ceramic coating layer is porous.

(14) The composite biotic implant of (13) wherein said ceramic coating layer is a porous one having an average pore diameter of 10 to 100 μm and a porosity of 10 to 70%.

(15) The composite biotic implant of any one of (1) to (14) wherein the ceramic material of which said particles or coating layer is formed is a bio-active, non-calcium phosphate series sintered ceramic material which has a composition comprising at least one of alkaline earth metal oxides and alkali metal oxides and $SiO_2$ and which can precipitate a calcium phosphate compound on a surface in an aqueous solution containing phosphorus.

(16) The composite biotic implant of any one of (1) to (15) wherein the ceramic material of which said particles are formed is of substantially the same type as the ceramic material of which said coating layer is formed.

(17) The composite biotic implant of (15) or (16) wherein said ceramic material is substantially free of phosphorus.

(18) The composite biotic implant of any one of (15) to (17) wherein said ceramic material has a composition comprising at least one alkaline earth metal oxide and $SiO_2$, the weight ratio of $SiO_2$ to alkaline earth metal oxide contents ranging from 1:4 to 6:1.

(19) The composite biotic implant of (18) wherein said alkaline earth metal oxide is at least one of CaO and MgO.

(20) A method for preparing a composite biotic implant as set forth in (1), comprising the steps of placing the ceramic particles on a surface layer of the metal substrate, and embedding the ceramic particles in said metal substrate by plastic working.

(21) The method for preparing a composite biotic implant of (20) wherein the plastic working is effected at 700° to 1200° C. and a pressure of 1 to 500 MPa.

(22) The method for preparing a composite biotic implant of (20) or (21), comprising the steps of placing the ceramic particles on a surface layer of the metal substrate, embedding the ceramic particles in said metal substrate by plastic working, and thereafter coating a bio-compatible ceramic material thereover.

ADVANTAGES

The present invention uses a highly plastic metal having high strength and ductility as the substrate in a surface of which ceramic particles are embedded by a metal plastic working process. The metal substrate and the ceramic particles are joined through mechanical engagement, achieving a very high bond strength which has never been achieved in the prior art. Differently stated, the ceramic particles do not leave the metal substrate unless the particles themselves are crushed. Since discrete ceramic particles are independently joined to the metal substrate, only some ceramic particles separately fall out even when separation occurs and it never happens that the coating layer peels off in "plane" cleavage as in the prior art.

Since ceramic particles are embedded in the metal substrate surface, the implant surface is embossed and toughened at the same time as junction, resulting in the anchoring effect of promoting initial fixation and neoblastic bone growth.

Moreover, in the embodiment in which an implant having ceramic particles embedded therein is surface coated with a biotic ceramic material, the spaces between ceramic particles are filled with the ceramic material, thus preventing the metal components from leaching out, resulting in further increased bio-compatibility, bio-affinity and bio-activity. In this embodiment, if the material of the ceramic particles and the material of the ceramic coating layer are of substantially the same type, the coating layer is integrally joined to the ceramic particles in mechanical engagement with the metal substrate, resulting in a significantly high bond strength.

Moreover, the embodiment in which the ceramic material of which the ceramic particles or ceramic coating layer is formed in the practice of the invention is one having a composition comprising at least one of alkaline earth metal oxides or alkali metal oxides and $SiO_2$ rather than calcium phosphate series sintered ceramic materials provides an implant with significantly high bio-activity and high strength.

ILLUSTRATIVE CONSTRUCTION

Figure 1:
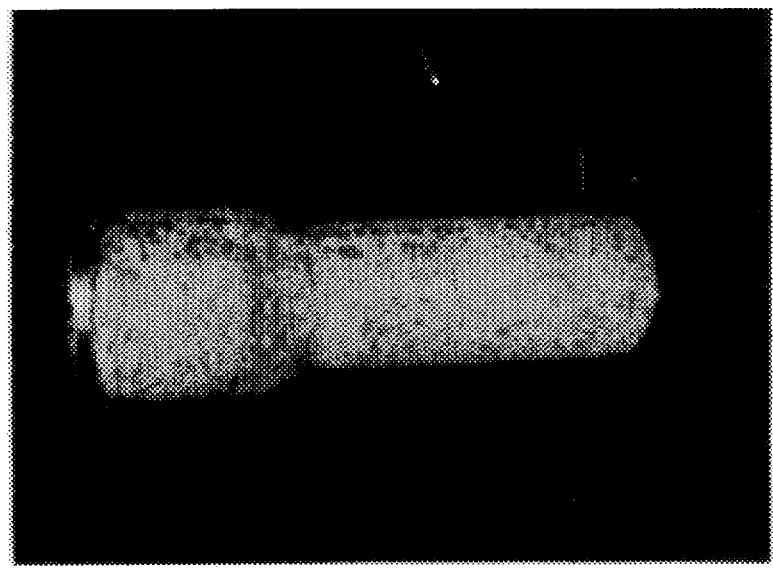
FIG. 1 is a photograph of a composite biotic implant according to the present invention embodied as a dental root, showing the structure of ceramic particles in the surface layer.

Now the construction of the present invention is described in detail. The implant of the present invention uses a highly plastic metal as a substrate and has ceramic particles embedded in a surface layer thereof by virtue of metal plasticity.

Metal Substrate

The highly plastic metal material used herein is not particularly limited insofar as it is not harmful to the living body, has a strength in excess of a certain level, for example, at least 500 MPa, and exhibits "high plasticity," that is, significant plasticity at or below the temperature at which strength is significantly reduced, for example, the temperature corresponding to 70% of the melting point. Preferred among others are highly plastic metal materials having a ductility of at least 50% at a temperature corresponding to 70% or less of its melting point and a pressure of 50 MPa. Most preferable are superplastic metal materials having a ductility of at least 200% under these conditions because a bond is more easily established between the metal and ceramic particles.

Preferred examples of the superplastic metal material include Ti and Ti base alloys containing up to 20% by weight in total of at least one element selected from the group consisting of Al, V, Fe, Mo, Cr, Zr, Pd, N, Si, and O, for example, Ti—6Al—4V (expressed in % by weight), Ti—Al—Sn, Ti—Pd, Ti—Mo, Ti—Zr, Ti—Fe, Ti—Al—V—Mo—Fe, Ti—Fe—N—O, Ti—Cr—Si, and Ti—Pd—Cr; Al base alloys such as Zn—22Al, Zn—21.5Al—0.01 Mg alloy (SPZ); stainless steel; and Ni base alloys. With respect to bio-compatibility, however, pure Ti (ductility about 200%) and Ti base alloys are preferred. The Ti and Ti alloys generally have a coefficient of thermal expansion $\alpha_1$ of approximately $8-10 \times 10^{-6}/°$ C.

It will be understood that the metal substrate can have a flat surface since it is deformed by the subsequent embedding process although it may have a previously toughened surface. The surface roughness prescribed in JIS B-0601 may range from the measurement lower limit to 300 μm.

Embodiment

The implant of the present invention is manufactured by embedding ceramic particles in a surface layer of the highly plastic metal substrate mentioned above. The technique used herein may be a "metal plastic working process" of applying heat and pressure to ceramic particles in contact with a metal substrate, thereby achieving embedment and joint by taking advantage of the plastic deformation of the metal. Inter alia, plastic (or superplastic), working of the aforementioned superplastic metal material is preferred.

The metal plastic working process may be performed by means of a conventional hot press (HP), hot isostatic press (HIP), warm isostatic press (WIP) or the like. HP is preferably used for implants of simple shape because of ease of operation and HIP and WIP are used for implants of complex shape.

The pressing temperature is generally in the range of from 200° to 1,200° C. and below the melting point of the metal material as the substrate. The pressure is preferably 1 to 500 MPa, more preferably 5 to 300 MPa, most preferably 5 to 100 MPa. The working time is generally from 1 to 600 minutes. The amount of deformation is generally at least 0.1, preferably about 1 to 3 as expressed in true strain of the overall substrate although it varies with the size of particles to be buried.

Plastic working is performed on a metal substrate of a predetermined shape which has been coated with grease, for example, over a necessary area and has ceramic particles closely adhered to the substrate. This working results in an implant for use as an artificial dental root having ceramic particles buried in the metal substrate surface as seen from the photographs of FIGS. 1 and 2.

Ceramic Particles

The ceramic particles used herein generally have a mean particle size of from 1 to 5,000 μm, preferably from 10 to 2,000 μm, more preferably from 30 to 300 μm. Within this range, plastic embedment is likely to occur. Too large particle sizes would render plastic embedment difficult and leave a larger space between particles, and larger particles result in an implant of larger dimensions. Too small particle sizes would render embedment operation difficult. The use of ceramic particles within the above-defined particle size range ensures the manufacture of implants having a desired surface roughness as will be described later.

Preferably, the ceramic particles have a particle size distribution as uniform as possible. Ceramic particles with a uniform particle size are embedded to a uniform depth (percent embedment), which leads to the uniformity of bond strength. It is to be noted that if relatively large particles are used, small particles may be used in combination to form a mixture having two or more particle size distributions. In this case, small particles intervene between large particles when embedded, imparting uniformity to the ceramic layer in a plane direction.

As to geometry, the ceramic particles should preferably have an average shape factor of up to 2, more preferably up to 1.5. As the shape factor increases, the shape becomes more irregular so that ceramic particles can be locally distributed on the substrate leaving sparse areas. For this reason, a shape factor approximate to unity is preferred. It is to be noted that the shape factor is the minimum diameter divided by the maximum diameter of a particle and the average shape factor is calculated by randomly picking up about 100 particles.

Further ceramic particles of spherical shape are preferred because the particles are slidingly displaced during pressing with the likelihood to form a ceramic layer which is even or uniform in a plane direction. Also after an implant is implanted in a living tissue, the ceramic layer free of extremely sharp edges does not cause unnecessary stimulation to the living body and is unlikely to absorb the bone. Inversely, if it is desired to enhance the anchoring effect of an implant to a living hard tissue such as bone for achieving firmer fixation, ceramic particles having sharp edges are preferably used.

Also preferably, the ceramic particles have a coefficient of thermal expansion $\alpha_1$ which is 0.5 to 1.5 times the coefficient of thermal expansion $\alpha_1$ of the metal substrate. This prevents breakage and falling off of ceramic particles during embedding process.

The ceramic particles used herein may be prepared by finely dividing sintered bodies, granulating by a pyrolytic spraying, tumbling granulation or fluidized bed process followed by sintering, forming particles by a liquid phase synthesis process using a solution followed by sintering, spray roasting/sintering, or tumbling layer or fluidized bed sintering.

Embodiment Layer

The embedment depth or percent embedment of ceramic particles is preferably in the range of 10 to 100%, more preferably 40 to 70% of the particle size. Since implants like artificial dental roots are subject to continuous stresses after implantation, a lower percent embedment would allow particles to fall out. A too higher percent embedment means that more metal areas are exposed between ceramic particles or the implant anchoring effect is reduced. The percent embedment may be calculated by observing a cross section of an implant under a microscope, randomly picking up 100 embedded particles, and determining the ratio of the embedment distance to the particle length in a direction normal to the substrate.

Further, the percent of the area of an implant coated with ceramic particles relative to the area of the implant in contact with a living hard tissue (biotic contact area), that is, coverage by ceramic particles is preferably at least 20%, more preferably at least 40%, most preferably 70 to 100%. It is preferred for bio-affinity or bio-activity that the biotic contact area be entirely formed by biotic ceramics.

It is to be noted that the process of embedding ceramic particles does not substantially deform the ceramic particles, but the metal substrate. The amount of deformation in a surface layer corresponds to the aforementioned percent embedment and is at least about 10% of the particle size. Since ceramic particles are not substantially deformed by the embedding process, an embedment layer is generally formed by a single layered arrangement of embedded particles.

The embedment layer of ceramic particles is generally 1 to 500 μm thick, preferably 5 to 120 μm thick. The thickness of the layer formed by embedded particles, that is, embedment layer may be calculated by taking a photomicrograph of the substrate having an irregular surface layer and determining the difference between an envelope tangent to the raised portions of the substrate and an envelope tangent to the top of embedded particles. A too thin embedment layer provides a weak anchoring effect so that a ceramic coating layer, if subsequently applied, would have low peel strength. A too thick embedment layer would be likely to peel off.

The embedment layer of ceramic particles should preferably have a surface roughness of 1 to 2,000 μm especially 10 to 300 μm (Ra defined by JIS B-0601). A too smooth embedment layer allows for slippage on the surface and provides little anchoring effect whereas a too rough embedment layer gives a reduced area of contact with the adjoining bone retarding the rate of integration.

It is thus believed that ceramic particles are not only firmly engaged in the metal substrate through a mechanical crimping structure, but also form a solid phase bond at the interface.

Ceramic Coating

If the metal substrate is not fully covered simply by embedding ceramic particles therein, or if it is desired to completely cover the metal substrate surface with ceramics, then a coating layer of ceramic material can be formed on the embedment layer of ceramic particles.

The ceramic coating layer can be formed by well-known techniques, for example, a coating technique of mixing ceramic powder with a binder to form a paste and applying and baking the paste, a thermal spraying technique, and vapor phase film deposition techniques including evaporation and sputtering.

The ceramic coating layer can have a strong bond strength which has never been achieved in the prior art because the ceramic coating layer overlies the embedment layer of ceramic particles firmly joined to the metal substrate and forms a ceramic-to-ceramic bond therewith.

The material of which the ceramic coating layer is formed is preferably a ceramic material of substantially the same type as the ceramic particles (a ceramic material based on the same main component), more preferably a ceramic material of the same composition as the ceramic particles in order to bond and integrate the coating layer with the ceramic particles for providing increased bond strength. The same main component means that two ceramic materials contain at least 30% by weight, especially at least 20% by weight, even at least 10% by weight of common components in a weight ratio of from about 1/3 to 3/1, especially from about 1/2 to 2/1 between the two.

The ceramic coating layer overlying the metal substrate generally has a total thickness of 1 to 5,000 µm, preferably 10 to 2,000 µm, more preferably 50 to 1,000 µm combined with the embedment layer. A too thin coating layer would be insufficient for the growth of neoblastic bone whereas a too thick coating layer would lead to a lowering of peel strength. This thickness is measured as the thickness between the previously mentioned envelope tangent to the raised portions of the metal substrate surface layer and an envelope tangent to the surface of the coating layer. Preferably in this embodiment, the coating layer is adjusted in thickness such that the surface irregularities defined by the embedment layer of ceramic particles are left behind. Namely, the implant of the invention preferably possesses the rough or irregular surface defined by the embedment layer of ceramic particles and the ceramic coating layer, when formed, should preferably reproduce this surface nature. When the implant is implanted in a living hard tissue, the irregular implant surface is effective for anchoring the implant to the living hard tissue accomplishing firm initial fixation. The irregular configuration presented by bio-affinity ceramic material promotes generation of neoblastic bone which will penetrate among the irregularities to interdigitate therewith, virtually accomplishing a firm fit. The implant on the outer surface has an average surface roughness Ra (JIS B-0601) of 1 to 2,000 µm, preferably 5 to 100 µm.

Further, bio-affinity is enhanced for promoting formation of neoblastic bone by providing the ceramic coating layer with pores to form a porous layer. Then osteoblasts and nutrient vessels will penetrate into pores in the implant surface to promote formation of neoblastic bone, leading to quicker curing.

The pores in the ceramic coating layer preferably have a mean pore diameter of 10 to 100 µm, more preferably 20 to 80 µm. The layer preferably has a porosity of 10 to 70%, more preferably 20 to 60%. A too small average pore diameter impedes entry of cells into pores, failing in quick curing. A too large pore diameter would lower strength and leave a too large gap around cells so that the pores become less effective. A too low porosity would be less effective for improving bio-affinity whereas a too high porosity would lower strength. It is to be noted that the pore diameter and porosity are calculated from an observation under a microscope or scanning electron microscope.

The ceramic coating layer can be provided with pores by various prior art well-known methods. For example, ceramic material powder is mixed with a pyrolyzable substance such as cellulose particles and reins particles corresponding to a desired particle diameter and porosity and further with a solvent and resin binder to form a paste, which is coated and baked to an implant. Baking of the ceramic paste causes the pyrolyzable substance particles in the paste to decompose and disappear, leaving pores corresponding to the particles.

The thus formed pores may have various structures depending on the type of pyrolyzable substance mixed. In the case of resin particles, for example, there are left relatively large pores conforming to the particle shape and narrow passage pores created by the escaping gases resulting from decomposition of the resin. In the case of crystalline cellulose or the like, interconnecting irregular pore paths are formed. The pyrolyzable substance particles used herein generally have a mean particle size of 10 to 100 µm, preferably 20 to 80 µm and are mixed in an amount of 10 to 70% by weight, preferably 30 to 60% by weight based on the weight of the ceramic paste.

Often, the ceramic coating layer baked to the metal substrate preferably has a mean grain size of 0.001 to 100 µm. For materials having a firing temperature of 1000° C. or higher, a mean grain size of 0.01 to 50 µm, especially 0.1 to 20 µm is preferred. For lower-temperature firing materials, a mean grain size of up to 1 µm, especially up to 0.1 µm is preferred. A too small grain size is difficult to achieve whereas a too large grain size would lower strength. It is to be noted that the grain size is determined by measuring the area of crystal grains by means of a scanning electron microscope (SEM) and calculating the average diameter on the assumption that the grains are circular.

Ceramic Material

Various materials may be used as the ceramic particles to be embedded in a surface layer of a highly plastic metal substrate and the ceramic coating layer. Exemplary are bio-active ceramic materials, for example, calcium phosphate series such as hydroxyapatite (HAP), tricalcium phosphate (TCP) and bio-glass; monocrystalline and polycrystalline alumina series; zirconia series; and non-calcium phosphate series such as diopside.

The implants intended for use as living body replacements or complements favor ceramic materials having bio-activity in a sense that newly grown neoblastic bone can directly bond with the ceramic material. Known as bio-active ceramic materials are calcium phosphate series ceramic materials to which bone is accessible, typically HAP, TCP and calcium fluoride (FAP).

However, more preferred are bio-active non-calcium phosphate series ceramic materials such as diopside which possess bio-activity and high strength and when indwelled in living tissues, allow bone to grow on a surface so that bonds are created from both the material and bone sides. These materials are sintered ceramic materials having a composition comprising at least one oxide of alkaline earth metal oxides and alkali metal oxides and $SiO_2$ and at the same time, non-calcium phosphate series sintered ceramic materials which are substantially free of phosphorus as a base component. Irrespective of the non-calcium phosphate system, these materials are biologically active and characterized in that upon contact with an aqueous solution containing phosphorus (e.g., spurious and true body fluids), they form calcium phosphate series compounds, typically hydroxyapatite (HAP) on their surfaces of contact.

Ceramic materials having bio-compatibility or bio-affinity are acceptable when medical instruments or implements to be indwelled in living bodies are contemplated. The bio-compatibility or bio-affinity means that bone can grow in contact with the ceramic material without leaving gaps. Since bio-activity is a special example of bio-compatibility, the bio-compatibility is used in this specification as encompassing bio-activity.

Almost all ceramic materials are useful as the bio-compatible ceramic materials, including oxide ceramic materials such as alumina, zirconia, silica, calcia, magnesia, and titania series materials, carbide series materials and nitride series materials. For medical instruments or implements to be indwelled in living bodies, these materials are applicable to both the ceramic particles to be embedded and the ceramic coating layer. For living hard tissue replacements or complements, these materials are applicable to the ceramic particles embedded which are covered with the ceramic coating layer. However, since the coating layer should preferably have bio-activity and the particles should preferably be of the same type of material, it is preferred that both the particles to be embedded and the coating layer are of a bio-active ceramic material which will be described below.

Bio-Active Composition

Typical of the bio-active ceramic material used herein is a composition comprising at least one member of alkaline earth metal oxides and alkali metal oxides and $SiO_2$ in a weight ratio of from 1:4 to 6:1, preferably from 1:3 to 2:1. Outside the range, bio-affinity or strength lowers.

This composition can be reduced in coefficient of thermal expansion by increasing the content of $SiO_2$ relative to the content of alkaline earth and alkali metal oxides. This will advantageously provide a matching in coefficient of thermal expansion between the ceramic material and the metal substrate as previously described (with the ratio therebetween ranging from 0.5 to 1.5). If the metal substrate is noticeably different from the ceramic material in coefficient of thermal expansion, the ceramic portion can be broken or damaged during metal plastic working or baking of the ceramic coating layer. Where a ceramic material is laminated on the metal substrate, its coefficient of thermal expansion $\alpha_1$ can be adjusted to the range of from $6.65 \times 10^{-6}$ to $12.35 \times 10^{-6}$ by controlling the content of $SiO_2$ in the range of 30 to 75% by weight, preferably 35 to 70% by weight of the entire ceramic composition.

In these cases, the alkaline earth metal oxide is one or two members selected from CaO, MgO, SrO, BaO, etc., with CaO and MgO being preferred.

CaO Essential Composition

Ceramic materials containing CaO containing a precipitating HAP component, among other alkaline earth metal oxides, as an essential component are preferred for bio-activity, strength and ease of manufacture. Useful are ceramic compositions containing 20 to 90% by weight, especially 30 to 70% by weight of CaO.

It is also possible to use CaO as an essential component and partially another alkaline earth metal oxide such as MgO, SrO and BaO. Especially, inclusion of MgO is preferred since it contributes to lower-temperature firing capability and the adjustment of coefficient of thermal expansion. In the composition represented by $xCaO.yMgO.2SiO_2$, increasing x will increase the coefficient of thermal expansion and increasing y will decrease the coefficient of thermal expansion. For example, the compositions of $CaO.2SiO_2$, $\frac{1}{2}CaO.\frac{1}{2}MgO.2SiO_2$, and $MgO.2SiO_2$ have an $\alpha_1$ of $10.0 \times 10^{-6}$, $9.5 \times 10^{-6}$, and $7.5 \times 10^{-6}$, respectively. The coefficient of thermal expansion can be adjusted in this way. The weight ratio of CaO to MgO preferably ranges from 1:10 to 100:0, especially from 1:10 to 10:1.

The content of MgO is preferably in the range of 0.1 to 60% by weight of the ceramic composition. For matching of coefficient of thermal expansion with such metals as Ti and lower-temperature firing capability, the content of MgO should be in the range of from 0.1 to 35% by weight. Materials mainly composed of CaO preferably have a composition comprising 10 to 88% by weight of CaO, 2 to 35% by weight of MgO, and 10 to 80% by weight of $SiO_2$, more preferably 18 to 47% by weight of CaO, 10 to 25% by weight of MgO, and 37 to 68% by weight of $SiO_2$.

CaO-Free Composition

At the beginning, we believed that the presence of CaO containing a HAP component is indispensable to form HAP on ceramics. Quite unexpectedly, our continuing study revealed that a compositional system free of CaO also has an ability to form HAP. This compositional system was found to be more bio-active than the conventional calcium phosphate series ceramics.

More particularly, it is possible to use instead of CaO, at least one metal oxide selected from other alkaline earth metal oxides, e.g., MgO, SrO and BaO and/or alkali metal oxides. Compositions substantially free of CaO are available in some cases. Where other alkaline earth metal oxides such as MgO, SrO and BaO are used, their content may range from 0.1 to 90% by weight of the ceramic composition and preferably their total content ranges from 20 to 90% by weight, especially from 30 to 70% by weight of the ceramic composition.

Alkali metal oxides may be used instead of the alkaline earth metal oxides or as a partial substitute therefor. In this case, one or more members are selected from $Na_2O$, $K_2O$ and $Li_2O$ and they are preferably used as an additive component to MgO and sometimes CaO.

The content of alkali metal oxides may range from 0.1 to 90% by weight of the ceramic composition and preferably their total content ranges from 0.1 to 70% by weight, especially up to 50% by weight of the ceramic composition from the standpoints of strength, bio-activity and matching of coefficient of thermal expansion.

Exemplary Composition Field

Figure 8:
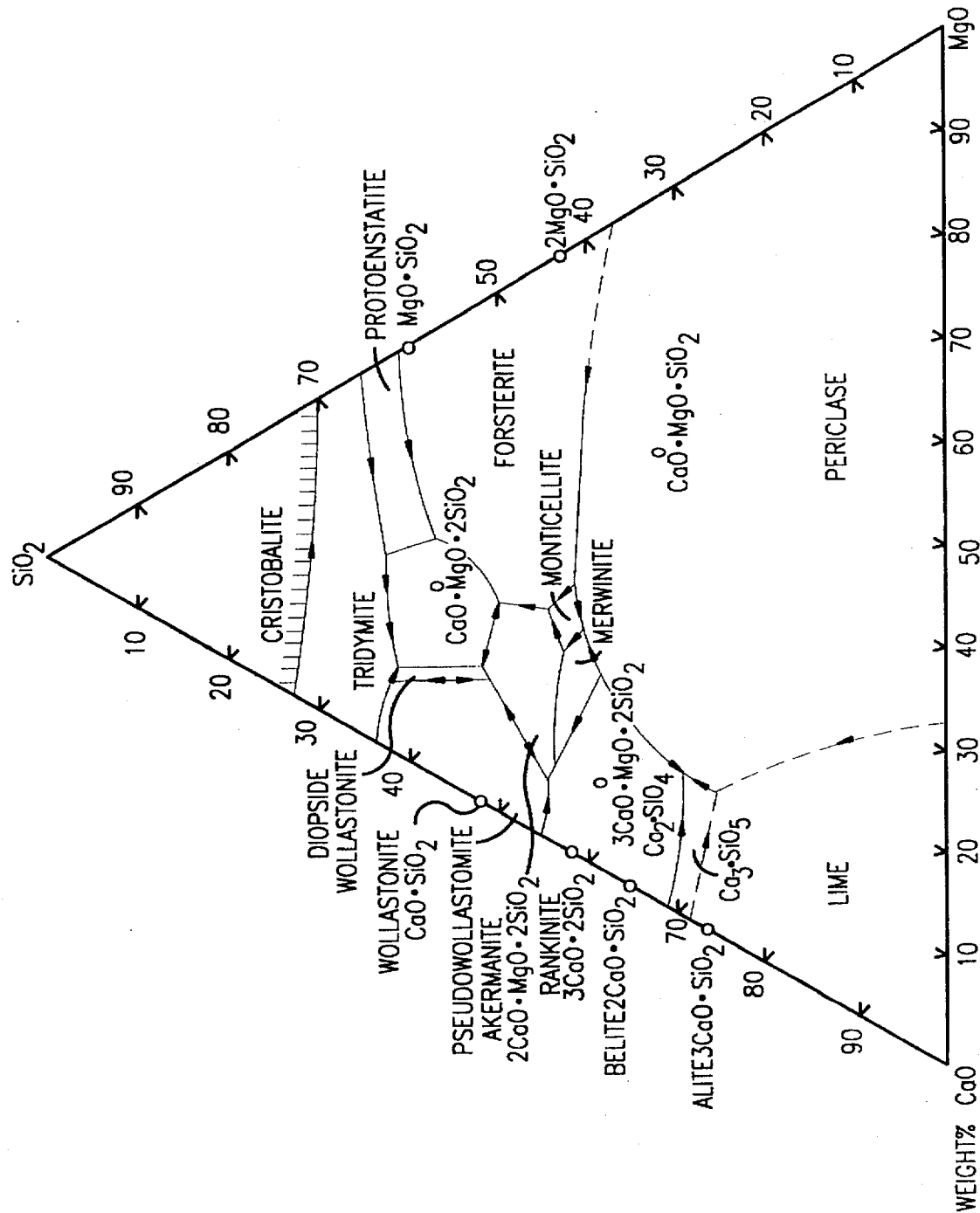
FIG. 8 is a ternary diagram of $SiO_2$—CaO—MgO system for explaining the composition of preferred ceramic material.

The ceramic materials used herein, if they are of material series containing alkaline earth metal oxides, are ceramic materials belonging to the fields of diopside: (Ca,Mg)O—MgO—2SiO_2, especially $2SiO_2$—CaO—MgO, wollastonite: β-(Ca,Mg)O—SiO_2, especially CaO—SiO_2, alite: $3CaO—SiO_2$ belite: $2CaO—SiO_2$, akermanite: $2CaO—MgO—2SiO_2$, monticellite: CaO—MgO-SiO_2, forsterite: 2(Mg,Ca)O—SiO_2, proteoenstatite: (Mg,Ca)O—SiO_2, tridymite: $SiO_2$ and so on. These fields are depicted in the ternary phase diagram of FIG. 8.

Preferred material series containing CaO as an essential component are those belonging to the diopside, wollastonite, alite, belite, akermanite, and monticellite fields, and among others, ceramic materials predominantly comprising those belonging to the diopside field and capable of firing at relatively low temperatures and those belonging to the wollastonite field are especially preferred with the additional benefit of high strength. In the case of the CaO-free material series, those belonging to the forsterite field are preferred. In addition to the ceramic materials belonging to the selected compositional fields, a mixture thereof with another compound as mentioned above is also useful.

Among material series containing alkali metal oxides are $SiO_2$—$K_2O$, $SiO_2$—LiO—MgO, $SiO_2O$—$Li_2O$—$TiO_2$, $SiO_2$—$TiO_2$—CaO, $SiO_2$—$Na_2O$ and similar compositional series. Those which can be sintered at low temperatures are $SiO_2$—$K_2O$ and $SiO_2$—$Na_2O$ series.

In addition to the aforementioned components, the ceramic materials which can be used herein may have blended therein an optional component such as $TiO_2$, ZnO, $B_2O_3$, FeO, and $ZrO_2$, if necessary, in an amount not impairing the desired physical properties. The bond strength of the ceramic material to the metal substrate can be increased by introducing an oxide of a metal substrate component such as $TiO_2$ into the ceramic material. It will be understood that inclusion of $Al_2O_3$ is less desirable because of its adverse influence on bio-activity.

Low-Temperature Firable Ceramic Material

According to the present invention, when a ceramic coating layer is laminated on an implant having ceramic particles buried therein by a baking process or the like, the temperature of firing the ceramic material should preferably be lower than the melting point of the substrate material.

The melting point of typical metal materials is 1,668° C. for metallic titanium, 1,650° C. for Ti—6Al—4V alloy, 1,400° C. for stainless steel, and 1,300° C. for nickel alloys. Therefore, the ceramic firing temperature is preferably up to 1,200° C., more preferably up to 1,000° C.

Low-temperature firing becomes possible by controlling the composition. Alternative useful methods are to increase the activity of ceramics by finely dividing raw material powder, and to mix low-melting glass frit with ceramic powder for lowering the firing temperature. These methods may be used separately, but preferably in combination.

The activity of ceramics can be increased by several methods, for example, by finely dividing raw material powder, and by treating ceramic raw material powder on the surface with acid for activation. The ceramic raw material powder generally has a BET converted particle size value of at least 0.1 $m^2/g$, and it is preferably comminuted to at least 5 $m^2/g$, especially 10 to 200 $m^2/g$ when low-temperature firing is necessary. Powder having a too large particle size or a too low BET value is less susceptible to low-temperature firing. Inversely, powder having a too small particle size or a too high BET value is difficult to manufacture. The ceramic material powder should be not only fine, but also uniform in order to provide increased activity.

Material powder as mentioned above may be treated with an acid such as hydrochloric acid prior to firing for increasing its surface activity.

Alternatively, ceramic powder is mixed with low-melting glass frit to form a matrix for lowering the firing temperature. In this method, ceramic powder is mixed with low-melting glass frit with the aid of a solvent such as water to form a paste, which is applied and fired to a substrate for firm bond. Although the addition of glass is effective for lowering the firing temperature, it tends to lower bio-activity. Therefore, the former methods of increasing the activity of ceramics are preferred for bio-activity.

The firing temperature in the last method is above the softening temperature of glass, usually 400° to 1,000° C. Examples of the glass include silica, borate, silicate, borosilicate and phosphate series, with the borosilicate glass being preferred because of appropriate treating temperature. The amount of glass blended is generally 5 to 80% by weight, preferably 15 to 60% by weight based on the total weight of the coating material. Adhesion would lower with a blending amount below the range whereas bio-activity would lower beyond the range.

Synthesis of Ceramic Material

The ceramic material powder used herein may be synthesized by dry and wet synthesis methods or the like as mentioned above. Preferred for producing fine uniform powder are a pyrolytic spraying method, liquid phase synthetic method such as co-precipitation and precipitation, alkoxide method, and sol-gel method.

More particularly, the pyrolytic spraying method is by atomizing an aqueous solution containing ceramic component ions adjusted to a desired composition with the aid of gas or a ultrasonic vibrator, and heating the droplets for synthesizing spherical, hollow, fine particles. The hollow particles may be ground for further increasing the BET value.

The co-precipitation method is by evenly mixing ceramic component ions in an aqueous solution state and allowing mixed components to chemically precipitate as a solid phase concurrently by virtue of differential solubility. There are obtained fine particles of high purity and at least 60 $m^2/g$.

The alkoxide method is by mixing a Ca alkoxide, a Si alkoxide and the like to form an alkoxide solution containing respective ceramic components, and subjecting the solution to hydrolysis reaction for synthesizing fine particles of high purity and high BET value.

The sol-gel method is by mixing selected components in aqueous solution form to form a sol, dewatering the sol into a gel, and calcining the gel into oxides.

Coating Method

The ceramic coating layer may be laminated onto the metal substrate, for example, by baking, thermal spraying or vapor phase film deposition techniques such as sputtering.

The baking method is by mixing the above-mentioned ceramic material powder with a binder component such as organic resins and a solvent component such as alcohols to form a paste, applying the paste to a metal substrate and firing it for baking. This creates a firm bond. The firing temperature is from 500° C. to the melting point of the metal substrate, preferably from 800° to 1,550° C., more preferably up to 1,400° C., and up to 1,200° C. especially for metal substrates having a low softening point.

The thermal spraying method is by melting ceramic material particles with a gas or plasma and causing the particles in atomized state to deposit on the substrate.

It is to be noted that when conventional HAP materials are deposited by thermal spraying, there arises a problem that the materials are likely to convert into TCP upon heating at high temperatures. Advantageously, the bio-active material series especially preferred in the present invention are unsusceptible to such conversion.

It is also possible to subject the surface of an intermediate layer or metal substrate to oxidizing treatment to form a metal oxide film.

Insofar as the aforementioned strength is not lost, the ceramic layer can be partially or entirely a porous layer having independent and interconnected pores. It is also possible to form a porous layer on a previously baked dense ceramic layer. This embodiment is effective for promoting retention of osteoblasts and passage of osteoblasts and blood, thereby promoting formation and integration of neoblastic bone.

EXAMPLE

Examples are given below by way of illustration.

Example 1

An artificial dental root substrate was prepared from pure metallic Ti having a ductility of at least 200% at the temperature (1,000° C.) corresponding to 70% of its melting point as superplastic metal material by shaping it to the shape shown in FIG. 1. The artificial dental root substrate was dimensioned to have a length of 13.5 mm, a root diameter (stem diameter) of 2.7 mm, and a cervical diameter (head diameter) of 3.7 mm and toughened on the surface by blasting (to Ra 35 μm).

Ceramic particles to be embedded were obtained by mixing 36.0% by weight of $CaCO_3$, 46.0% by weight of $SiO_2$ and 18.0% by weight of MgO in a conventional manner, calcining the mixture at 1,000° C., milling, compacting, and then firing at 1,280° C. The fired product was ground in an alumina mortar and classified through screens to collect dense diopside ($CaO.2SiO_2.MgO$) particles having a mean particle size of 250 to 300 μm. The diopside particles had a compression strength of 200 MPa and a coefficient of thermal expansion of $10 \times 10^{-6}/°$ C., which is 1.0 times the coefficient of thermal expansion of the Ti metal substrate equal to $9.7 \times 10^{-6}/°$ C.

Figure 5:
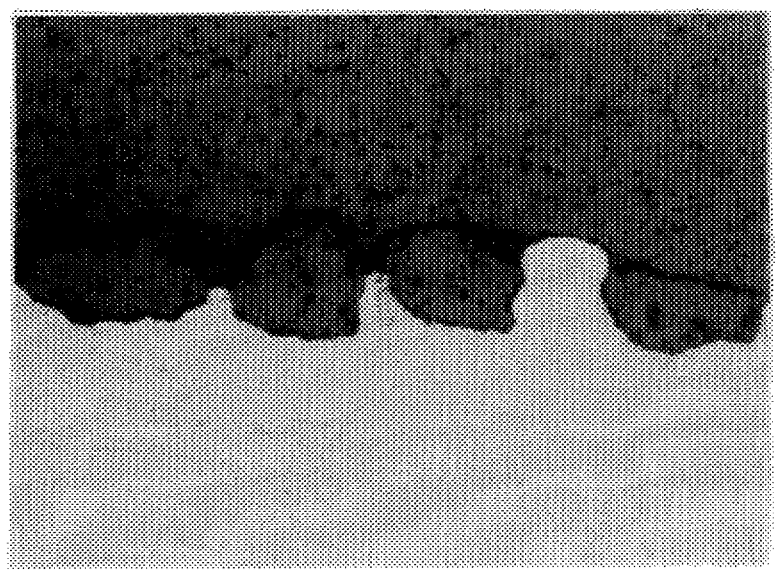
Figure 9:
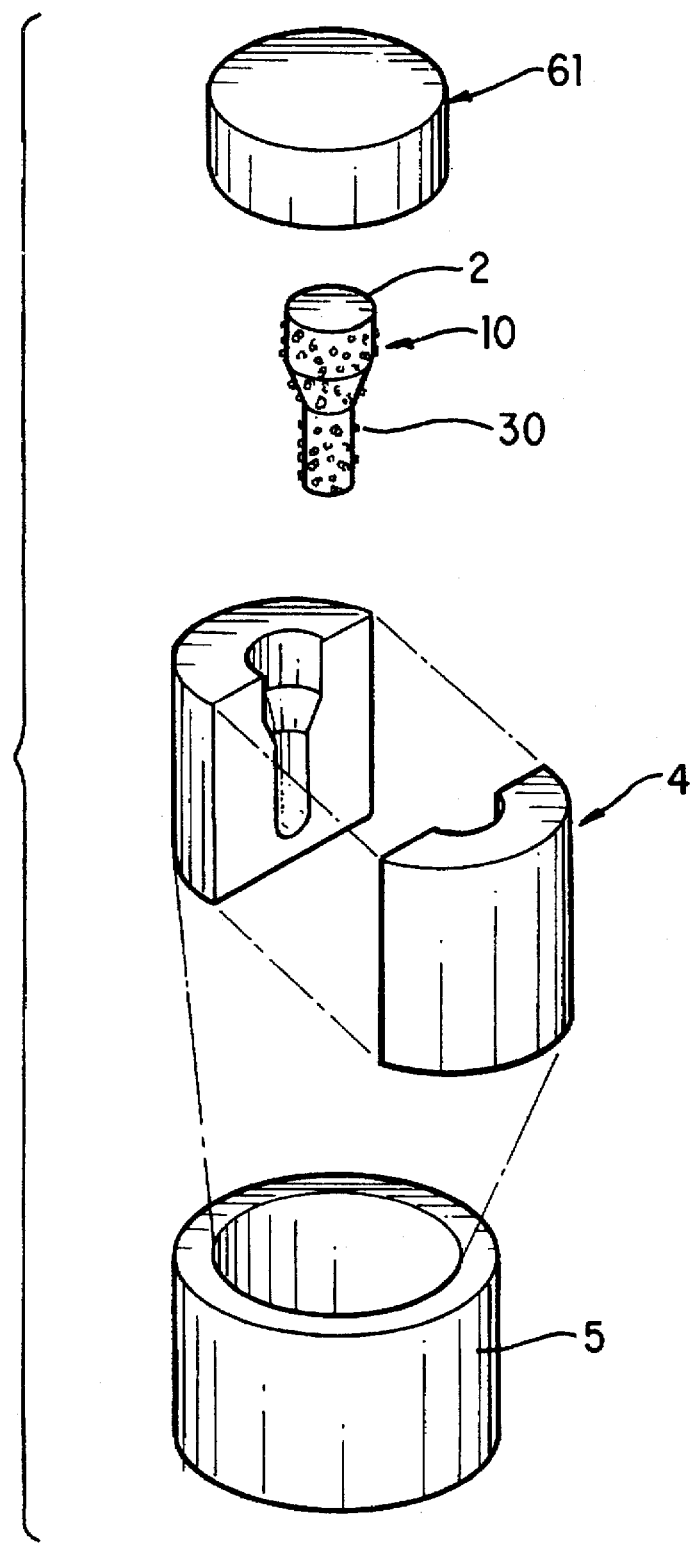
FIGS. 9 and 10 illustrate a method for preparing a composite biotic implant according to the present invention, FIG. 9 being an exploded perspective view and FIG. 10 being a partially cross-sectional elevation.
Figure 10:
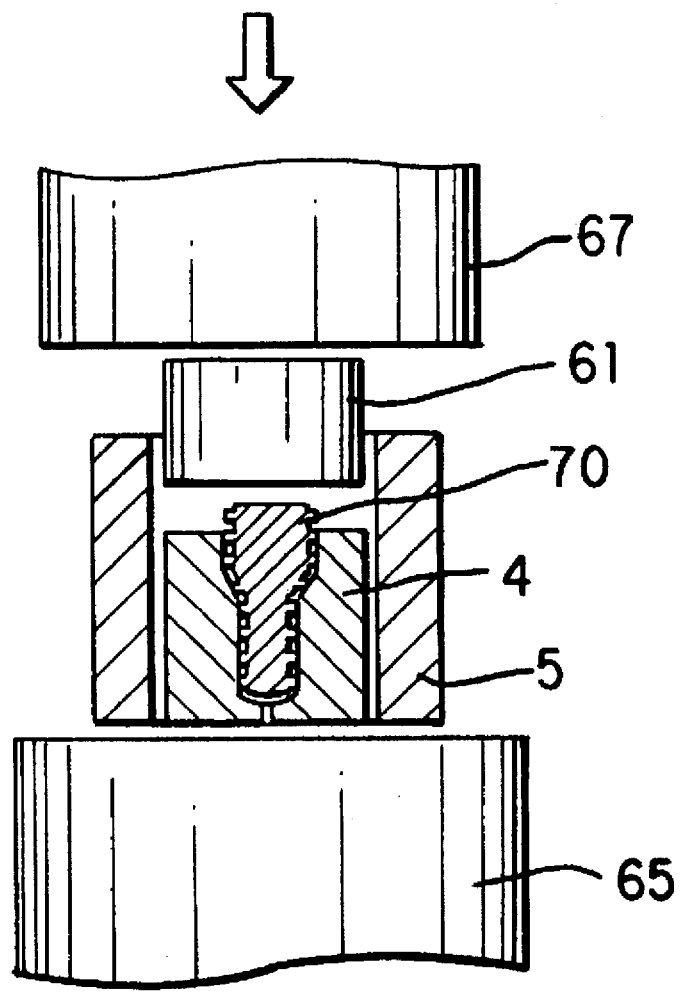

Next, as shown in FIG. 9, high vacuum grease was applied to the surface of Ti substrate 2 and ceramic particles 30 of the above-mentioned diopside were closely adhered to the entire side and bottom surfaces of substrate 2. Hot pressing was effected in an axial direction by means of an alumina mold for radially extending the metal substrate for providing plastic working. The mold assembly used is shown in FIGS. 9 and 10 as including a split mold 4 received in a cylindrical sleeve 5, upper and lower punches 61 and 65 disposed above and below the split mold 4, and press means 67 for pressing the punches 61 and 65 against each other. Pressing was conducted by first heating the sample 10 fitted in the mold at 950° C. for one hour, and then applying a pressure of 15 MPa for 30 minutes while heating. There was obtained an artificial dental root sample generally shown in the photographs of FIGS. 1 and 2. It is to be noted that these photographs are surface photographs of Example 5 which is described later. A section of the sample obtained in Example 1 is shown in the photograph of FIG. 5.

Example 2

An artificial dental root sample was fabricated by the same procedure as Example 1 except that the ceramic particles to be embedded had a mean particle size of 125 to 150 μm.

Example 3

An artificial dental root sample was fabricated by the same procedure as Example 1 except that the ceramic particles to be embedded were of wollastonite. The wollastonite particles were obtained by mixing 57.0% by weight of $CaCO_3$, 43.0% by weight of $SiO_2$ and 0% by weight of MgO along with a binder and solvent, calcining the mixture at 1000° C., milling, compacting, and then firing at 1,400° C. The fired product was ground in an alumina mortar and classified through screens to collect dense wollastonite ($CaO.SiO_2$) particles having a mean particle size of 250 to 300 μm. The wollastonite particles had a compression strength of 180 MPa and a coefficient of thermal expansion of $11 \times 10^{-6}/°$ C., which is 1.1 times the coefficient of thermal expansion of the metal substrate.

Example 4

An artificial dental root sample was fabricated by the same procedure as Example 1 except that the ceramic particles to be embedded were of hydroxyapatite.

The hydroxyapatite particles were obtained by synthesizing hydroxyapatite according to a hydrolysis method, compacting, firing at 1,300° C., grinding and classifying, thus collecting dense hydroxyapatite particles having a mean particle size of 250 to 300 μm. The hydroxyapatite particles had a compression strength of 80 MPa and a coefficient of thermal expansion of $12 \times 10^{-6}/°$ C., which is 1.3 times the coefficient of thermal expansion of the metal substrate.

Example 5

A Ti—6Al—4V alloy rod (having a coefficient of thermal expansion of $12 \times 10^{-6}/°$ C.) having a ductility of at least 200% at the temperature (750° C.) corresponding to 70% of its melting point as superplastic metal material was shaped into a metal substrate dimensioned as in Example 1 and subjected to similar surface toughening (to Ra 20 μm).

Figure 2:
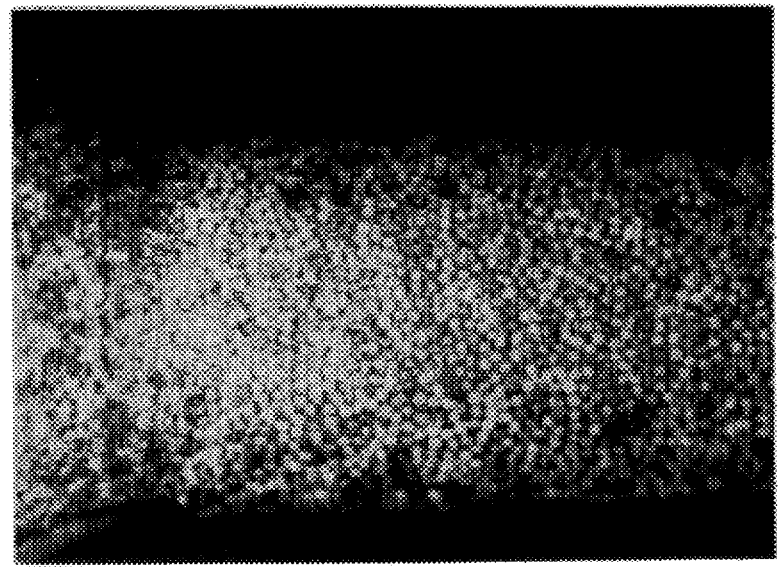
FIG. 2 is an enlarged photograph of FIG. 1.
Figure 3:
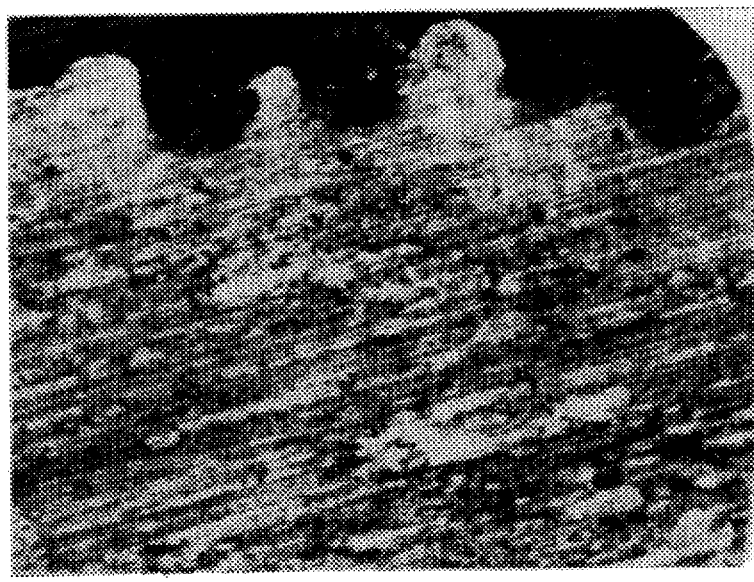
FIGS. 3, 4, 5, 6, and 7 are photomicrographs of a cross section of the surface layer of the dental root, showing ceramic particles embedded in the metal substrate, FIG. 7 being an enlarged photograph of FIG. 6.
Figure 4:
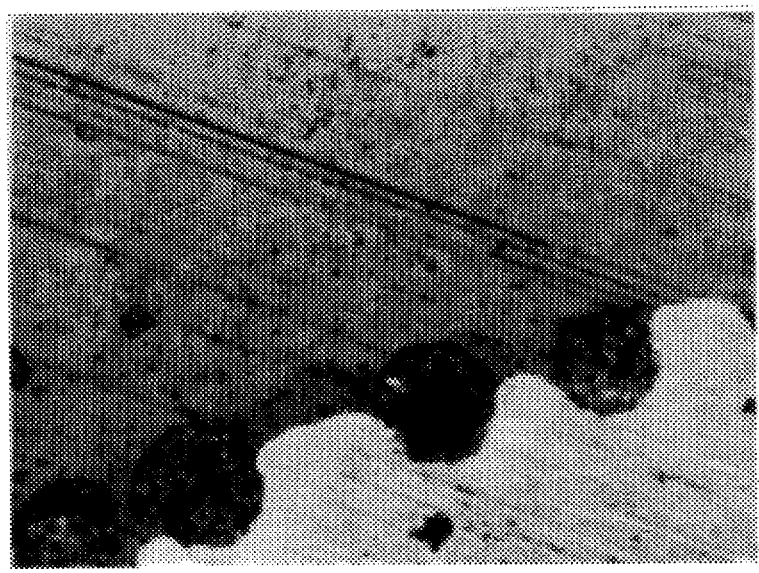

Diopside powder of the same composition as in Example 1 was mixed with a binder and solvent, granulated by a tumbling granulation technique, and fired at 1,280° C. The fired granules were classified to collect generally spherical, dense diopside ($CaO.2SiO_2.MgO$) particles having a mean particle size of 125 to 150 μm and a shape factor of up to 1.5. The diopside particles had a compression strength of 220 MPa and a coefficient of thermal expansion of $10 \times 10^{-6}/°$ C., which is 0.83 times the coefficient of thermal expansion of the metal substrate. A sample was fabricated through plastic working as in Example 1. FIGS. 1 and 2 are photographs showing the surface of the sample and FIGS. 3 and 4 are photographs showing a section thereof.

Example 6

To the surface of the artificial dental root sample obtained in Example 1, diopside particles of the same composition as the particles embedded therein were plasma sprayed to form a coating layer of 20 μm thick, obtaining an artificial dental root sample having a coverage of 100%.

Example 7

To the surface of the artificial dental root sample obtained in Example 1, a low-temperature firable diopside material paste was applied. After application, the coating was forced in between granules by CIP (cold isostatic press) and thereafter baked to form a coating layer of 20 μm thick, obtaining an artificial dental root sample having a coverage of 100%. The low-temperature firable diopside material was obtained by treating a diopside composition consisting of 25.9% by weight of CaO, 55.5% by weight of $SiO_2$ and 18.6% by weight of MgO by an alkoxide method into a uniform fine powder having a specific surface area (BET) of at least 150 $m^2/g$, and mixing the powder with a binder and solvent to form a paste. The firing temperature was 950° C.

Figure 6:
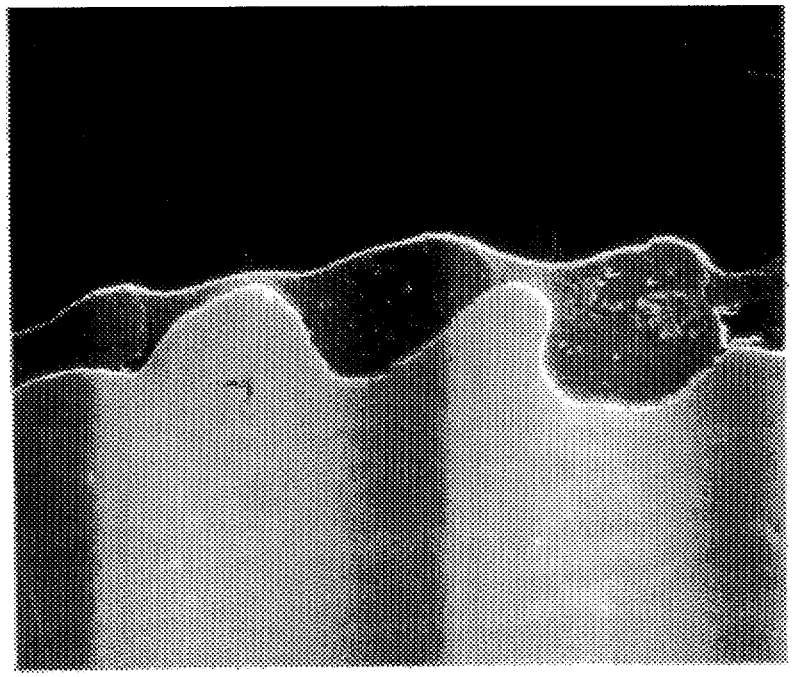
Figure 7:
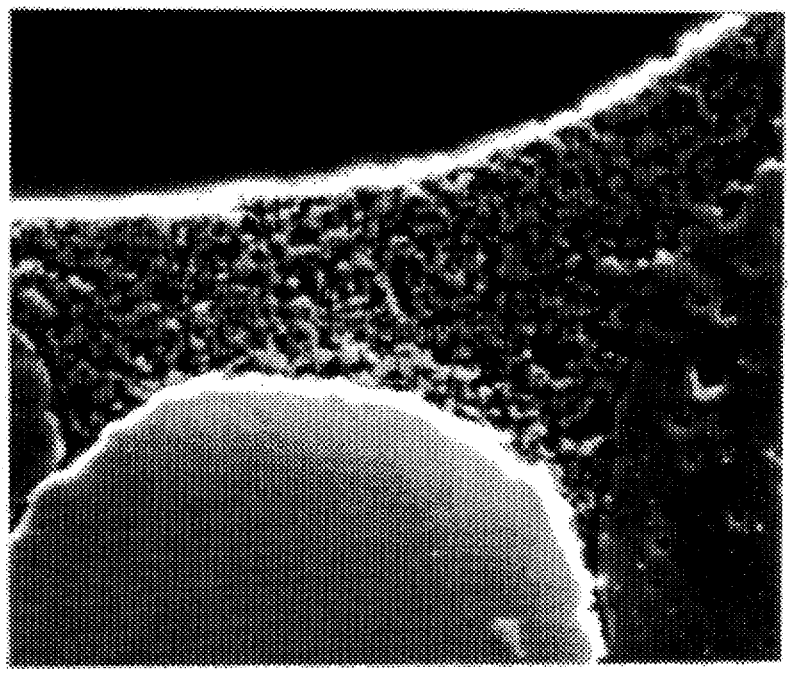

FIG. 6 is a photograph showing a section of the sample and FIG. 7 is an enlarged photograph thereof.

Example 8

To the surface of the artificial dental root sample having hydroxyapatite particles embedded in Example 4, hydroxyapatite of the same composition were plasma sprayed to form a coating layer of 200 μm thick, obtaining an artificial dental root sample having a coverage of 100%.

Example 9

The low-temperature firable diopside material paste used in Example 7 was mixed with 40% by weight of crystalline cellulose having a mean particle size of 50 μm. The low-temperature firable diopside material paste was applied to the surface of the artificial dental root sample obtained in Example 1 and baked to form a coating layer of 200 μm thick. The coating layer had continuous pores having an average pore diameter of 50 μm at a porosity of about 40% as a result of pyrolysis and burning off of the crystalline cellulose during baking, obtaining an artificial dental root sample having a porous coating layer.

Comparative Example 11

A coating layer of 200 μm thick was formed on the metal substrate used in Example 5 by plasma spraying the same material under the same conditions as in Example 5, but without superplastic embedment of ceramic particles. There was obtained an artificial dental root sample having a coverage of 100%.

Comparative Example 12

A coating layer of 200 μm thick was formed on the metal substrate used in Example 8 by plasma spraying the same material under the same conditions as in Example 8, but without superplastic embedment of ceramic particles. There was obtained an artificial dental root sample having a coverage of 100%.

The artificial dental root samples of Examples 1–9 and Comparative Examples 11–12 were tested for the state of ceramic material formed, bond strength, and bio-activity.

The state of ceramic material formed was examined by measuring the Ra of the embedment layer or coating layer of each sample according to JIS B-0601. The percent embedment of ceramic particles, the thickness of the embedment layer, percent coverage, and the total thickness of the embedment layer plus coating layer were calculated from sectional photomicrographs by the previously described methods.

Figure 11:
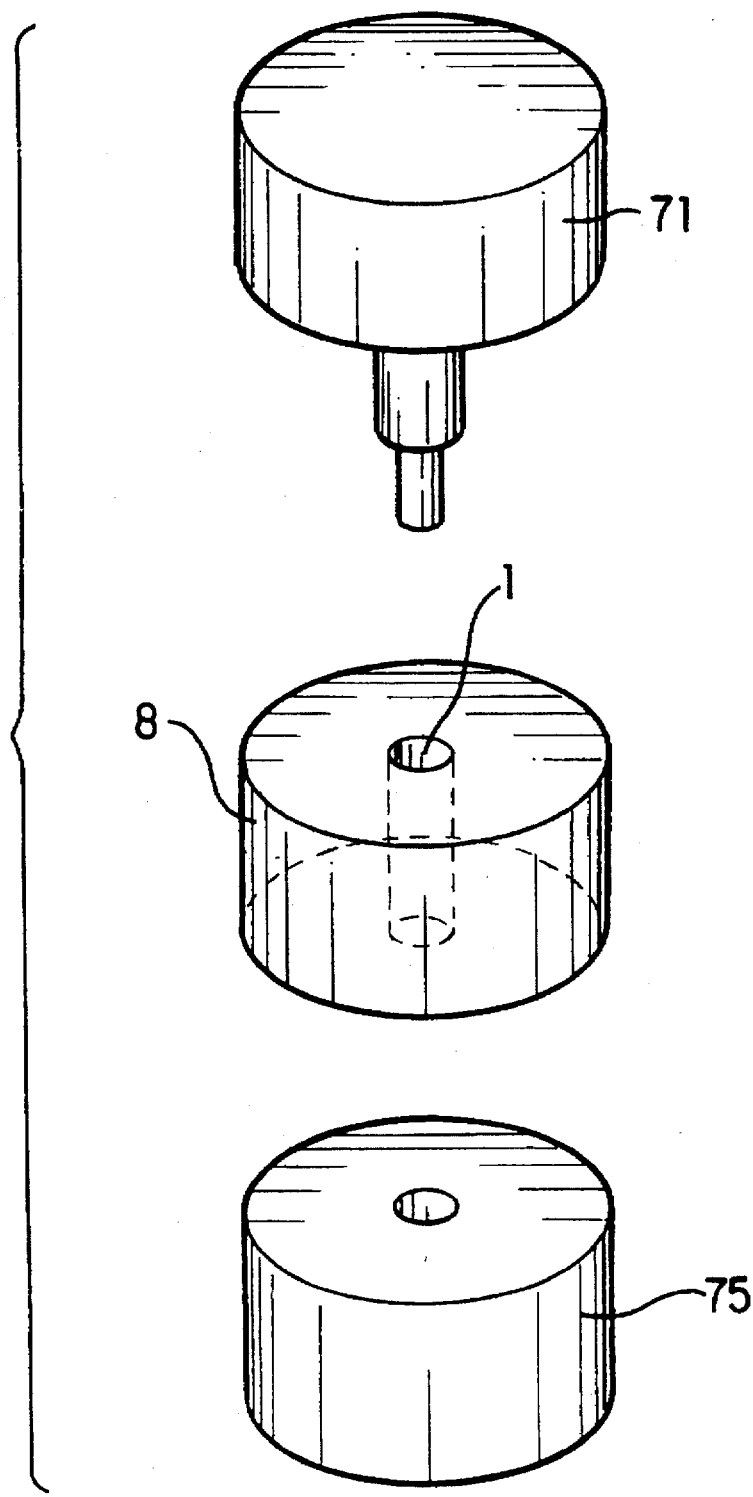
FIGS. 11 and 12 illustrate a method for measuring the peel strength of a composite biotic implant of the present invention, FIG. 11 being an exploded perspective view and FIG. 12 being a partially cross-sectional elevation.
Figure 12A:
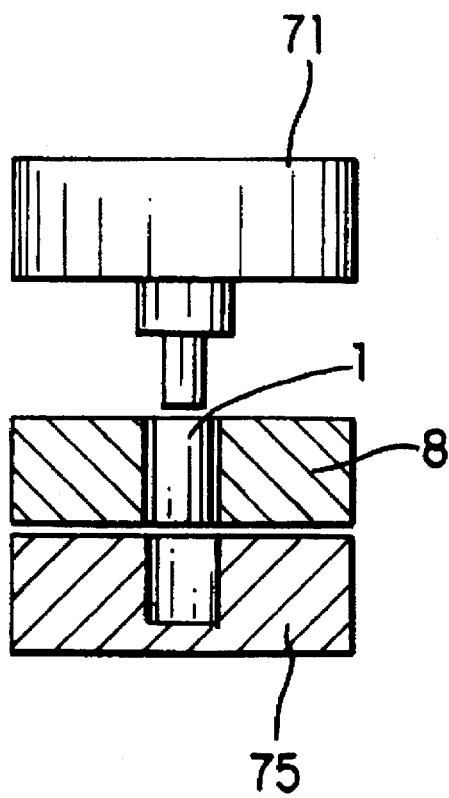
Figure 12B:
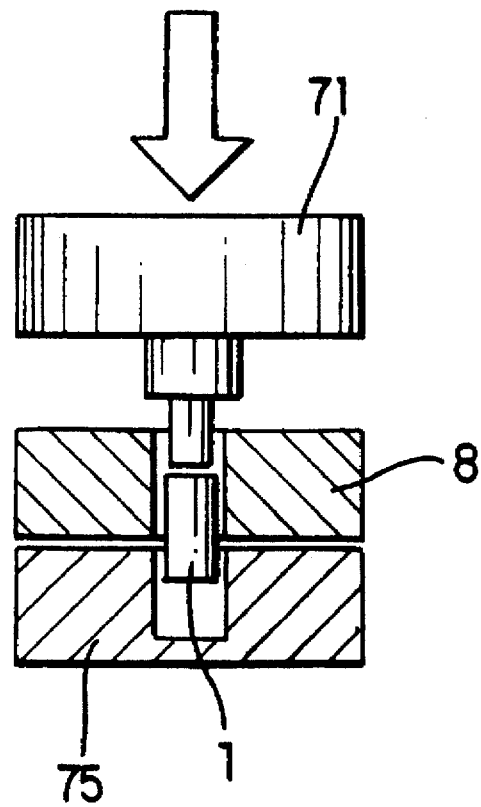

The peel strength was determined as shown in FIGS. 11 and 12 by inserting a sample 1 through an epoxy resin 8 with its opposite end surfaces exposed, pressing the sample 1 between upper and lower punches 71 and 75, and measuring the peel initiation pressing force at which initially embedded ceramic particles were left in the resin 8 or the coating layer was separated in plane cleavage. The samples of Examples 6 to 10 in which the coating layer was formed on the substrate through the embedment layer were subject to separation over very small areas at the peel initiation pressing force as compared with the samples of Comparative Examples 11 and 12. For the samples of Examples 1 to 5 having the embedment layer only, some discrete particles separated off and the area of the particles separated at the peel initiation pressing force was very small. The results are shown in Table 1.

As is evident from Table 1, the samples of the present invention were found to afford a substantially firm bond between the metal substrate and the ceramic material. As mentioned above, the samples of Comparative Examples 11 and 12 having only the thermally sprayed layer were low in bond strength and susceptible to plane peeling. The ceramic particles embedded according to the invention did not separate except when particles themselves fractured. Higher bond strength were achieved with diopside and wollastonite which in ceramic material form have higher strength than hydroxyapatite.

The bio-activity test was to observe whether or not hydroxyapatite (HAP) precipitated on sample surface when each sample was immersed in a spurious body fluid for 3 weeks. Then, no HAP precipitation was observed for the samples of Examples 1–3, 5–7 and 9. No metal ion leaching out was observed in the samples of Examples.

The artificial dental root samples were implanted in openings perforated in the jaw bones of rabbits. The jaw bones were removed 12 weeks later and prepared into specimens which were observed in section to find that the newly grown bone had penetrated into irregularities and pores in the surface of diopside and wollastonite and formed direct bond therewith providing integration. No separation was found between the metal substrate and the ceramic particles.

We claim:

1. A composite biotic implant prepared by a process comprising:

placing ceramic particles made of diopside, wollastonite or combination thereof, having a mean particle size ranging from 1 to 5,000 μm and having an average shape factor of up to 2 on a surface layer of a metal substrate; and embedding said ceramic particles in the metal substrate to the extent of 40–75% of the ceramic particle size by plastic working, thereby forming an embedment layer, said composite implant having a surface roughness Ra ranges from 1 to 2,000 μm.

2. The composite biotic implant of claim 1, wherein said metal of said metal substrate has a ductility of at least 50% at a temperature corresponding to 70% or less of its melting point.

3. The composite biotic implant of claim 1, wherein said ceramic particles exhibit bio-compatibility.

4. The composite biotic implant of claim 1, wherein said ceramic particles exhibit bio-affinity.

TABLE 1

| | Ceramic particles | | Embedment (%) | Embedment layer thickness (μm) | Ceramic coating layer composition | Embedment layer + coating layer total thickness (μm) | Average surface roughness Ra (μm) | Coverage (%) | Peel Strength (MPa) |
|---|---|---|---|---|---|---|---|---|---|
| | composition | Mean particle size (μm) | | | | | | | |
| E1 | Diopside | 250–300 | 65 | 90 | — | — | 50 | 70 | 450 |
| E2 | Diopside | 125–150 | 70 | 40 | — | — | 25 | 65 | 530 |
| E3 | Wollastonite | 250–300 | 55 | 130 | — | — | 80 | 70 | 400 |
| E4 | HAP | 250–300 | 50 | 140 | — | — | 85 | 70 | 300 |
| E5 | Diopside | 125–150 | 75 | 40 | — | — | 20 | 65 | 650 |
| E6 | Diopside | 250–300 | 65 | 90 | Diopside | 110 | 15 | 100 | 450 |
| E7 | Diopside | 250–300 | 65 | 90 | Diopside | 90 | 40 | 100 | 550 |
| E8 | HAP | 250–300 | 50 | 140 | HAP | 300 | 25 | 100 | 350 |
| E9 | Diopside | 250–300 | 65 | 90 | Diopside | 250 | 35 | 100 (porous) | 300 |
| CE11 | — | — | — | — | Diopside | 200 | 15 | 100 | 220 |
| CE12 | — | — | — | — | HAP | 200 | 20 | 100 | 120 |

5. The composite biotic implant of claim 1, wherein the coverage of the biotic contact surface of the metal substrate with said ceramic particles is at least 20%.

6. The composite biotic implant of claim 1, wherein said ceramic particles have a coefficient of thermal expansion which is lower than the coefficient of thermal expansion of the metal substrate multiplied by a factor of 0.5 to 1.5.

7. The composite biotic implant of claim 1, wherein a layer of a bio-compatible ceramic material is coated over the embedment layer.

8. The composite biotic implant of claim 7, wherein said embedment layer and said coating layer have a combined thickness of 1 to 5,000 μm.

9. The composite biotic implant of claim 7, wherein the ceramic material of said coating layer is a bio-active, phosphate sintered ceramic material which has a composition prepared from $SiO_2$ and at least one oxide selected from the group consisting of alkaline earth metal oxides and alkali metal oxides and which can precipitate a calcium phosphate compound on a surface from an aqueous solution containing phosphate.

10. The composite biotic implant of claim 7, wherein the ceramic material of which said coating layer is formed is diopside, wollastonite or combination thereof.

11. The composite biotic implant of claim 9, wherein said ceramic material of the coating layer is substantially free of phosphorous.

12. The composite biotic implant of claim 9, wherein said ceramic material of the coating layer has a composition prepared from alkaline earth metal oxide and $SiO_2$, the weight ratio of $SiO_2$ to alkaline earth metal oxide ranging from 1:4 to 6:1.

13. The composite biotic implant of claim 12, wherein said alkaline earth metal oxide is at least one member selected from the group consisting of CaO and MgO.

14. The composite biotic implant of claim 1, wherein said plastic working is effected at 700° to 1,200° C. and at a pressure of 1 to 500 MPa.

15. The composite biotic implant of claim 7, wherein said coating layer is a porous ceramic coating layer which has an average pore diameter of 10 to 100 μm and a porosity of 10 to 70%.

16. The composite biotic implant of claim 1, wherein said ceramic particles are embedded in said metal substrate to the extent of 40–70% of said particle size.

* * * * *